United States Patent
McNitt-Gray et al.

(10) Patent No.: US 10,058,302 B2
(45) Date of Patent: Aug. 28, 2018

(54) METHOD TO REDUCE RADIATION DOSE IN MULTIDETECTOR CT WHILE MAINTAINING IMAGE QUALITY

(75) Inventors: Michael F. McNitt-Gray, Culver City, CA (US); Di Zhang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 857 days.

(21) Appl. No.: 13/811,219

(22) PCT Filed: Jul. 20, 2011

(86) PCT No.: PCT/US2011/044704
§ 371 (c)(1),
(2), (4) Date: Apr. 2, 2013

(87) PCT Pub. No.: WO2012/012549
PCT Pub. Date: Jan. 26, 2012

(65) Prior Publication Data
US 2013/0188770 A1    Jul. 25, 2013

Related U.S. Application Data

(60) Provisional application No. 61/366,339, filed on Jul. 21, 2010.

(51) Int. Cl.
*A61B 6/00* (2006.01)
*A61B 6/03* (2006.01)

(52) U.S. Cl.
CPC ............... *A61B 6/542* (2013.01); *A61B 6/03* (2013.01); *A61B 6/035* (2013.01); *A61B 6/545* (2013.01);
(Continued)

(58) Field of Classification Search
CPC ....... A61B 6/542; A61B 6/5217; A61B 6/661; A61B 6/032; A61B 6/4085; A61B 6/563;
(Continued)

(56) References Cited

U.S. PATENT DOCUMENTS 5,459,329 A    10/1995 Sinclair
5,873,826 A    2/1999 Makoto et al.
(Continued)

FOREIGN PATENT DOCUMENTS

GB    2351554 A    1/2003

OTHER PUBLICATIONS

Johnson M K et al, Retrographic sensing for the measurement of surface texture and shape, 2009 IEEE Conference on Computer Vision and Pattern Recognition, Miami Beach Florida USA, Jun. 20, 2009, pp. 1070-1077, XP03607061, ISBN: 978-1-4244-3992-8.
(Continued)

*Primary Examiner* — Dani Fox
(74) *Attorney, Agent, or Firm* — Foley & Lardner LLP; Cliff Z. Liu

(57) ABSTRACT

A method of reducing radiation dose for a selected organ on a patient in a computed tomography (CT) scan that uses an X-ray source to scan the patient. The method comprises a computer determining a tube start angle for the X-ray source of the CT scan based on a location of the selected organ, a starting location of the X-ray source, a beam width of the CT scan, and a pitch of the CT scan. The starting angle of the X-ray source of the CT scan can then be set based on the determined tube start angle. In some embodiments, the organ location, X-ray starting location, beam width, and pitch are used to determine the number of tube rotations from the X-ray starting location to the organ location. This tube rotation number can be used to determine the tube start angle.

26 Claims, 13 Drawing Sheets

(52) U.S. Cl.
CPC ............ *A61B 6/488* (2013.01); *A61B 6/5217* (2013.01); *A61B 6/547* (2013.01); *A61B 6/583* (2013.01)

(58) Field of Classification Search
CPC ........... A61B 6/03; A61B 6/035; A61B 6/488; A61B 6/545; A61B 6/547; A61B 6/583; A61L 36/488; A61L 36/542; A61L 36/545; A61L 36/547
USPC .................................................. 378/4, 5, 16
See application file for complete search history.

(56) References Cited

U.S. PATENT DOCUMENTS

| | | |
|---|---|---|
| 2001/0019599 A1 | 9/2001 | Guendel |
| 2004/0116797 A1* | 6/2004 | Takahashi ............... A61B 6/032 600/407 |
| 2006/0140335 A1* | 6/2006 | Heuscher ............... G06T 11/006 378/4 |
| 2007/0098140 A1 | 5/2007 | Tsujii et al. |
| 2008/0191864 A1 | 8/2008 | Wolfson |
| 2008/0318679 A1 | 12/2008 | Tran et al. |
| 2009/0024030 A1* | 1/2009 | Lachaine ............. A61B 8/0825 600/437 |
| 2009/0189874 A1 | 7/2009 | Chene et al. |
| 2010/0035688 A1 | 2/2010 | Picunko |
| 2010/0152619 A1 | 6/2010 | Kalpaxis et al. |
| 2010/0222711 A1 | 9/2010 | Lajeunesse |
| 2011/0095197 A1* | 4/2011 | Forthmann ............. A61B 6/032 250/393 |

OTHER PUBLICATIONS

Nagata K et al, Feature detection with an image based compliant tactile sensor, Proceedings of the 1999 | EEE/RSJ International Conference on Intelligent Robots and Systems. (IROS '99). Human and Environmental Friendly Robots With Intelligence and Emotional Quotients, Kyongju, Korea Oct. 17, 1999, pp. 838-843, XP002175226, ISBN 978-0-783-5185-1.

International Search Report and Written Opinion for International Application No. PCT/US2011/044704, dated Feb. 24, 2012, 9 pages.

* cited by examiner

Table IV. The maximum organ dose reduction for several pregnant female phantoms, under all the simulated pitch values and collimation settings.

| Organ | Collimation 28.8mm | | Collimation 40mm | |
|---|---|---|---|---|
| | Pitch 1.5 | Pitch 0.75 | Pitch 1.5 | Pitch 0.75 |
| F24 (5 weeks) Ges sac | 12% | 5% | 17% | 8% |
| F10 (7 weeks) Ges Sac | 12% | 5% | 18% | 6% |
| F7 (12 weeks) fetus | 11% | 2% | 18% | 5% |
| F31 (19 weeks) fetus | 1% | 1% | 3% | 3% |

Table I. Age, gender and size descriptions of the 3 models

| Model | Age | Gender | Weight (kg) | Height (cm) |
| --- | --- | --- | --- | --- |
| Baby | 8 weeks | Female | 4.2 | 57 |
| Child | 7 years | Female | 21.7 | 115 |
| Irene | 32 years | Female | 51 | 163 |

Fig. 11

Table II. The size, gestational age and related information for studied pregnant female phantoms

| Model | Gestational Age (week) | Uterine Length (cm) | Studied regions | | |
| --- | --- | --- | --- | --- | --- |
| | | | Uterus | Gestational sac | Fetus |
| F26 | 5 | 7 | √ | √ | - |
| F10 | 7 | 6 | √ | √ | - |
| F7 | 12 | 7.5 | √ | √ | √ |
| F31 | 19 | 18.25 | √ | √ | √ |

Fig. 12

Table III. The maximum dose reduction for all the studied organs for GSF phantoms, under all simulated pitch values and collimation settings.

|  | Collimation 28.8mm | | | Collimation 40mm | | |
|---|---|---|---|---|---|---|
| Organ | Pitch 1.5 | Pitch 1.0 | Pitch 0.75 | Pitch 1.5 | Pitch 1.0 | Pitch 0.75 |
| Baby breast | 32% | 8% | 20% | 33% | 10% | 22% |
| Baby ovaries | 11% | 7% | 7% | 10% | 7% | 8% |
| Baby testes | 26% | 9% | 14% | 28% | 9% | 16% |
| Baby thyroid | 20% | 4% | 8% | 22% | 7% | 12% |
| Baby uterus | 8% | 5% | 5% | 9% | 6% | 7% |
| Baby eye lens | 38% | 3% | 15% | 41% | 6% | 21% |
| Child ovaries | 8% | 3% | 3% | 10% | 3% | 3% |
| Child testes | 33% | 6% | 11% | 36% | 9% | 16% |
| Child thyroid | 20% | 3% | 4% | 25% | 6% | 8% |
| Child uterus | 11% | 3% | 4% | 13% | 4% | 5% |
| Child eye lens | 49% | 7% | 20% | 51% | 8% | 23% |
| Irene breasts | 4% | 3% | 3% | 8% | 3% | 5% |
| Irene ovaries | 4% | 3% | 3% | 6% | 2% | 3% |
| Irene thyroid | 4% | 3% | 3% | 17% | 1% | 6% |
| Irene uterus | 4% | 2% | 2% | 8% | 2% | 2% |
| Irene eye lens | 52% | 11% | 17% | 54% | 13% | 22% |

Fig. 13

METHOD TO REDUCE RADIATION DOSE IN MULTIDETECTOR CT WHILE MAINTAINING IMAGE QUALITY

CROSS-REFERENCE TO RELATED APPLICATIONS

This application claims priority to U.S. Provisional Application Ser. No. 61/366,339, filed Jul. 21, 2010, entitled "METHOD TO REDUCE RADIATION DOSE IN MULTIDETECTOR CT WHILE MAINTAINING IMAGE QUALITY," which is hereby incorporated by reference as if set forth herein.

STATEMENT OF FEDERALLY SPONSORED RESEARCH OR DEVELOPMENT

This invention was made with Government support under EB004898, awarded by the National Institutes of Health. The Government has certain rights in the invention.

FIELD OF THE INVENTION

The present invention relates to the field of medical imaging. More particularly, the present invention relates to a method of reducing radiation dose in a multidetector computed tomography (CT) scan.

BACKGROUND OF THE INVENTION

The number of CT exams performed on patients has dramatically increased during the past few years, which has resulted in a higher risk of developing cancer for the patients due to the radiation dose received during the CT scans. Radiation dose to patients continues to be a significant concern to medical physicists and to the broader medical community as well. Radiation dose from CT exams has been identified as the largest source of medical radiation exposure. The knowledge of radiation dose to individual organs in the body is currently considered as the optimal means to estimate patient dose from CT.

Various approaches have been developed to reduce radiation dose from CT scans to patients, including tube current modulation (TCM), adjusting/lowering mAs for patient size, and lowering kVp (especially for studies using iodinated contrast), all while maintaining the diagnostic image quality that is so important in CT. These techniques have been very effective at reducing overall radiation dose to the patient. However, they have not been very anatomically specific, nor have they targeted specific radiation sensitive organs for radiation dose reduction. These approaches have been based on the overall size and shape (and other characteristics, such as the attenuation of the X-ray beam by the body) of the patient, and therefore have sought to reduce the overall radiation dose to the patient.

SUMMARY OF THE INVENTION

The present invention reduces the radiation dose to selected organs during a conventional helical CT scan performed on a patient. It provides a much more specific reduction in the radiation dose to radiation-sensitive organs that are exposed during a helical CT scan. The present invention is especially effective at reducing the radiation dose to small organs on small patients, such as the fetus on pregnant patients at an early gestational stage, or the lens of eyes on adult patients, among others.

In one aspect of the present invention, a method of reducing radiation dose for a selected organ on a patient in a computed tomography (CT) scan that uses an X-ray source to scan the patient is provided. The method comprises a computer determining a tube start angle for the X-ray source of the CT scan based on a location of the selected organ, a starting location of the X-ray source, a beam width of the CT scan, and a pitch of the CT scan.

In some embodiments, determining the tube start angle comprises the step of determining a number of tube rotations based on the location of the selected organ, the starting location of the X-ray source, the beam width of the CT scan, and the pitch of the CT scan, wherein the number of tube rotations is the number of tube rotations from the starting location of the X-ray source to the location of the selected organ. In some embodiments, the number of tube rotations is determined using the equation $R=(OLoc-SLoc)/(pitch \times N)$, wherein R is the number of tube rotations from the starting location of the X-ray source to the location of the selected organ, OLoc is the location of the selected organ centroid along a longitudinal axis, SLoc is the starting location of the X-ray source along a longitudinal axis, pitch is the pitch of the CT scan, and N is the beam width of the CT scan.

In some embodiments, the tube start angle is determined using a number of tube rotations, wherein the number of tube rotations is the number of tube rotations from the starting location of the X-ray source to the location of the selected organ. In some embodiments, the tube start angle is determined using the equation $TSA=OCTA-(360 \times (R-\text{floor}(R)))$, wherein TSA is the tube start angle, OCTA is the angle of the X-ray source of the CT scan as it crosses the longitudinal center of the selected organ, R is the number of tube rotations from the starting location of the X-ray source to the location of the selected organ; and floor(R) is the integer part of R. In some embodiments, the method further comprises determining the number of tube rotations R based on the location of the selected organ, the starting location of the X-ray source, the beam width of the CT scan, and the pitch of the CT scan. In some embodiments, the number of tube rotations R is determined using the equation $R=(OLoc-SLoc)/(pitch \times N)$, wherein OLoc is the location of the selected organ centroid along a longitudinal axis, SLoc is the starting location of the X-ray source along a longitudinal axis, pitch is the pitch of the CT scan, and N is the beam width of the CT scan.

In some embodiments, the method further comprises the step of setting the starting angle of the X-ray source of the CT scan based on the determined tube start angle. In some embodiments, the location of the selected organ, the starting location of the X-ray source, the beam width of the CT scan, and the pitch of the CT scan are input into the computer using a graphical interface. In some embodiments, the location of the selected organ is determined using a planning radiograph of the patient.

In another aspect of the present invention, a system for reducing radiation dose for a selected organ on a patient in a computed tomography (CT) scan that uses an X-ray source to scan the patient comprises a computer configured to determine a tube start angle for the X-ray source of the CT scan based on a location of the selected organ, a starting location of the X-ray source, a beam width of the CT scan, and a pitch of the CT scan.

In some embodiments, the computer is configured to determine the tube start angle by determining a number of tube rotations based on the location of the selected organ, the starting location of the X-ray source, the beam width of the CT scan, and the pitch of the CT scan, wherein the number of tube rotations is the number of tube rotations from the starting location of the X-ray source to the location of the selected organ.

In some embodiments, the computer is configured to determine the number of tube rotations using the equation R=(OLoc−SLoc)/(pitch×N), wherein R is the number of tube rotations from the starting location of the X-ray source to the location of the selected organ, OLoc is the location of the selected organ centroid along a longitudinal axis, SLoc is the starting location of the X-ray source along a longitudinal axis, pitch is the pitch of the CT scan, and N is the beam width of the CT scan.

In some embodiments, the computer is configured to determine the tube start angle using a number of tube rotations, wherein the number of tube rotations is the number of tube rotations from the starting location of the X-ray source to the location of the selected organ. In some embodiments, the computer is configured to determine the tube start angle using the equation TSA=OCTA−(360×(R−floor(R))), wherein TSA is the tube start angle, OCTA is the angle of the X-ray source of the CT scan as it crosses the longitudinal center of the selected organ, R is the number of tube rotations from the starting location of the X-ray source to the location of the selected organ, and floor(R) is the integer part of R. In some embodiments, the computer is configured to determine the number of tube rotations R based on the location of the selected organ, the starting location of the X-ray source, the beam width of the CT scan, and the pitch of the CT scan. In some embodiments, the computer is configured to determine the number of tube rotations R using the equation R=(OLoc−SLoc)/(pitch×N), wherein OLoc is the location of the selected organ centroid along a longitudinal axis, SLoc is the starting location of the X-ray source along a longitudinal axis, pitch is the pitch of the CT scan, and N is the beam width of the CT scan.

In some embodiments, the computer is configured to set the starting angle of the X-ray source of the CT scan based on the determined tube start angle. In some embodiments, the system further comprises a CT scanner communicatively coupled to the computer and configured to perform the CT scan of the patient. In some embodiments, the computer is configured to provide a graphical interface that enables a user to input the location of the selected organ, the starting location of the X-ray source, the beam width of the CT scan, and the pitch of the CT scan.

In yet another aspect of the present invention, a program storage device readable by a machine, tangibly embodying a program of instructions executable by the machine to perform a method of reducing radiation dose for a selected organ on a patient in a computed tomography (CT) scan that uses an X-ray source to scan the patient is provided. The method comprises determining a tube start angle for the X-ray source of the CT scan based on a location of the selected organ, a starting location of the X-ray source, a beam width of the CT scan, and a pitch of the CT scan In some embodiments, determining the tube start angle comprises the step of determining a number of tube rotations based on the location of the selected organ, the starting location of the X-ray source, the beam width of the CT scan, and the pitch of the CT scan, wherein the number of tube rotations is the number of tube rotations from the starting location of the X-ray source to the location of the selected organ. In some embodiments, the number of tube rotations is determined using the equation R=(OLoc−SLoc)/(pitch×N), wherein R is the number of tube rotations from the starting location of the X-ray source to the location of the selected organ, OLoc is the location of the selected organ centroid along a longitudinal axis, SLoc is the starting location of the X-ray source along a longitudinal axis, pitch is the pitch of the CT scan, and N is the beam width of the CT scan.

In some embodiments, the tube start angle is determined using a number of tube rotations, wherein the number of tube rotations is the number of tube rotations from the starting location of the X-ray source to the location of the selected organ. In some embodiments, the tube start angle is determined using the equation TSA=OCTA−(360×(R−floor(R))), wherein TSA is the tube start angle, OCTA is the angle of the X-ray source of the CT scan as it crosses the longitudinal center of the selected organ, R is the number of tube rotations from the starting location of the X-ray source to the location of the selected organ, and floor(R) is the integer part of R. In some embodiments, the method further comprises determining the number of tube rotations R based on the location of the selected organ, the starting location of the X-ray source, the beam width of the CT scan, and the pitch of the CT scan. In some embodiments, the number of tube rotations R is determined using the equation R=(OLoc−SLoc)/(pitch×N), wherein OLoc is the location of the selected organ centroid along a longitudinal axis, SLoc is the starting location of the X-ray source along a longitudinal axis, pitch is the pitch of the CT scan, and N is the beam width of the CT scan.

In some embodiments, the method further comprises the step of setting the starting angle of the X-ray source of the CT scan based on the determined tube start angle.

BRIEF DESCRIPTION OF THE DRAWINGS

FIG. 11 is a table of age, gender, and size descriptions of three different phantoms used in a study in accordance with some embodiments of the present invention.

FIG. 12 is a table of fetal age, size of the uterus, and studied regions for different pregnant female phantoms used in a study in accordance with some embodiments of the present invention.

FIG. 13 is a table of the maximum dose reduction for all the studied organs for GSF phantoms under different simulated pitch values and collimation settings in accordance with some embodiments of the present invention.

DETAILED DESCRIPTION

Figure 1A:
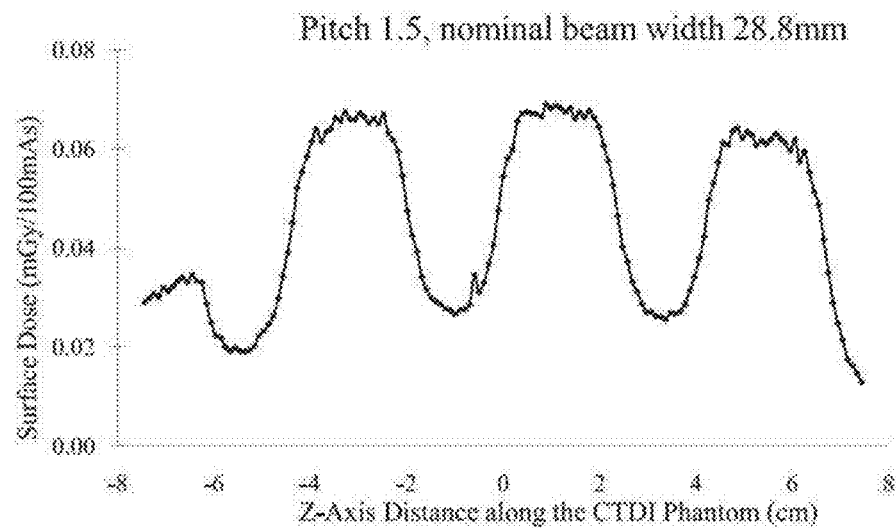
FIGS. 1A-B illustrate radiation dose patterns at the surface of a CTDI phantom when performing a CT scan in accordance with some embodiments of the present invention.

The following description is presented to enable one of ordinary skill in the art to make and use the invention and is provided in the context of a patent application and its requirements. Various modifications to the described embodiments will be readily apparent to those skilled in the art and the generic principles herein can be applied to other embodiments. Thus, the present invention is not intended to be limited to the embodiment shown, but is to be accorded the widest scope consistent with the principles and features described herein.

In some embodiments, the steps of the present invention are embodied in machine-executable instructions. These instructions can be used to cause a general-purpose or special-purpose processor that is programmed with the instructions to perform the steps of the present invention. Alternatively, the steps of the present invention might be performed by specific hardware components that contain hardwired logic for performing the steps, or by any combination of programmed computer components and custom hardware components.

The present invention can be provided as a computer program product that can include a machine-readable medium having stored thereon instructions that can be used to program a computer (or other electronic devices) to perform a process according to the present invention. The machine-readable medium can include, but is not limited to, ROMs, RAMs, magnet or optical cards, or other type of media/machine-readable medium suitable for storing electronic instructions.

Various aspects of the disclosure are described through the use of flowcharts. Often, a single instance of an aspect of the present disclosure is shown. As is appreciated by those of ordinary skill in the art, however, the protocols, processes, and procedures described herein can be repeated continuously or as often as necessary to satisfy the needs described herein. Additionally, it is contemplated that process steps can be performed in a different order than the order illustrated in the flowcharts unless otherwise disclosed, either explicitly or implicitly.

Furthermore, it is contemplated that any features from any embodiment can be combined with any features from any other embodiment. In this fashion, hybrid configurations of the disclosed embodiments are well within the scope of the present invention.

When helical CT scans are performed, the X-ray source rotates continuously around the patient as the patient table is translated through the X-ray gantry, resulting in a very rapid coverage of patient anatomy for the purposes of forming a series of images. From the patient's frame of reference, the X-ray source appears to move around the patient in the pattern of a helix, hence the name for helical CT scanning. The helical motion of the X-ray source produces a pattern of radiation on the surface of the patient that is periodic in nature (i.e., it is repeating) and in which the magnitude of variation can be quite high (i.e., the difference between the peaks and valleys of this surface dose pattern can be quite large). In contrast, the radiation pattern at the central portion of the patient (i.e., the part that is more at depth) is relatively constant. Therefore, this periodic radiation dose pattern at the surface of the patient can result in regions where the radiation dose is much higher in some locations ("hot spots") and much lower in other locations ("cold spots"), resulting in differences from maximum to minimum that can be as much as a factor of two or larger. There are significant dose variations with a sinusoidal pattern on the peripheral or surface of either a CTDI 32 cm phantom or an anthropomorphic phantom when helical CT scanning is performed, resulting in the creation of "hot" spots or "cold" spots. The inventors of the present invention have investigated the effectiveness of exploiting these variations to reduce the radiation dose to selected radiosensitive organs solely by varying the tube start angle in CT scans.

One commonly used metric to evaluate risk from radiation is the effective dose, calculated from a weighted average of absorbed dose to individual radiosensitive organs as defined by the International Commission on Radiological Protection (ICRP). While effective dose is very useful, a better method to estimate risk is to estimate the radiation dose to specific radiosensitive organs, which can be used in biological models to estimate the probability of radiation-induced carcinogenesis and genetic effects.

The surface dose distribution resulting from helical scanning of either a standard dosimetry phantom (e.g., a 32 cm CTDI phantom) or an anthropomorphic phantom is periodic. The period is influenced by the actual radiation beam width and table travel/movement. The magnitude of the variation in dose can be large, with maximum values greater than twice the minimum values under some conditions (e.g., with pitch=1.5). This magnitude of variation has been found in both homogenous cylindrical phantoms and heterogeneous anthropomorphic phantoms.

FIG. 1A illustrates the radiation dose pattern at the surface of a standard homogeneous radiation dosimetry phantom, known as a CTDI phantom, when performing a helical scan of pitch 1.5 with a nominal beam width of 28.8 mm and an actual beam width of 34.1 mm. This figure demonstrates the variation in the radiation dose at the surface, as well as its periodic pattern and the magnitude of the difference between the maximum (or peak) and the minimum (or valley), which is approximately a factor of 2 in this case.

Figure 1B:
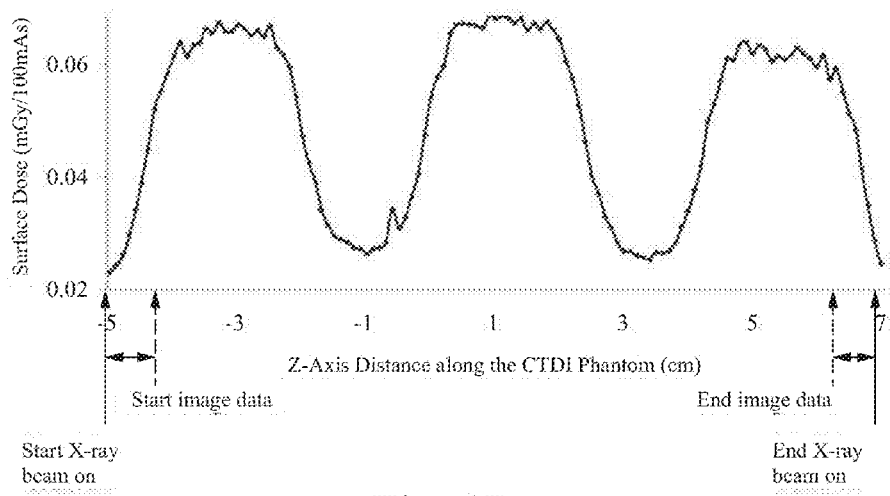

FIG. 1B illustrates the longitudinal dose distribution at the surface of a CTDI 32 cm phantom along the z-axis when performing a CT scan using a pitch of 1.5 and a nominal beam width of 28.8 mm. FIG. 1B also shows the region where the X-ray beam turns on and off, as well as the beginning and end of image data collection. Double-headed arrows indicate regions of overscan. The shape of the dose variation appears as a sinusoidal function because of the rotation of the CT tube, creating "cold spots" along the z-axis. As the tube start angle changes, the distribution of these spots will "move" along the z-axis.

Figure 2A:
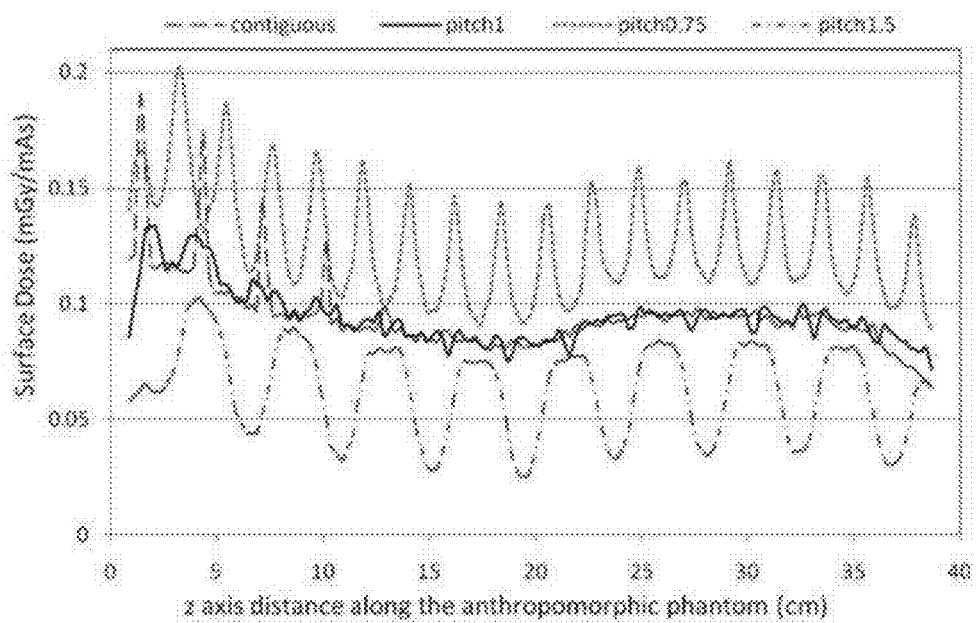
FIG. 2A illustrates the surface dose profile for an anthropomorphic phantom when simulated scans are performed at different pitches in accordance with some embodiments of the present invention.
Figure 2B:
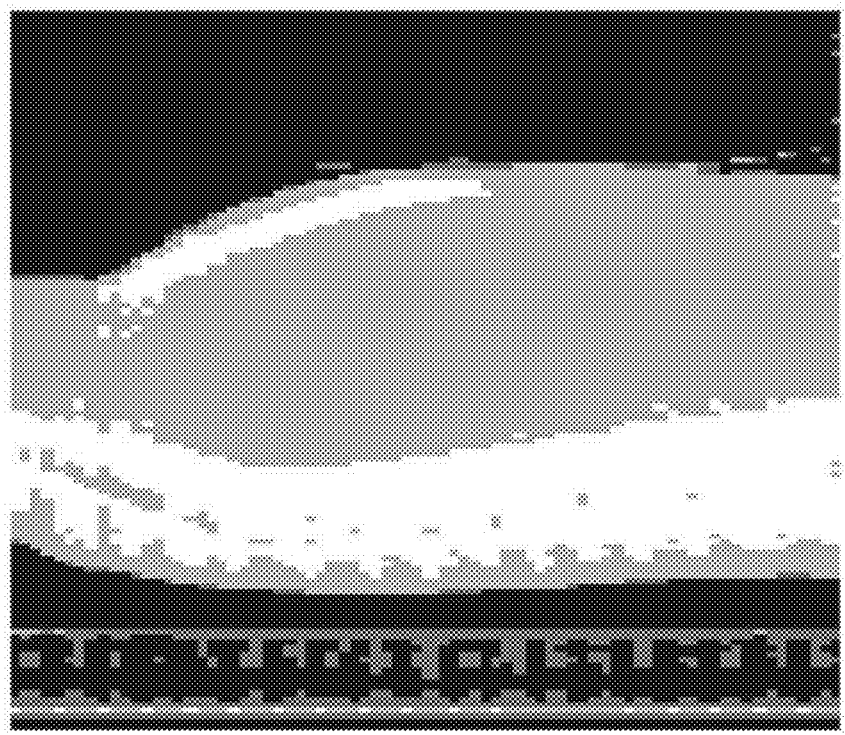
FIG. 2B illustrates the central sagittal plane of the phantom of FIG. 2A in accordance with some embodiments of the present invention.

FIG. 2A illustrates the surface dose profile for an anthropomorphic phantom when simulated scans are performed at pitch 0.75, pitch 1, and pitch 1.5, as well as a contiguous axial scan. FIG. 2B illustrates the central sagittal plane of the phantom.

Figures 3, 14:
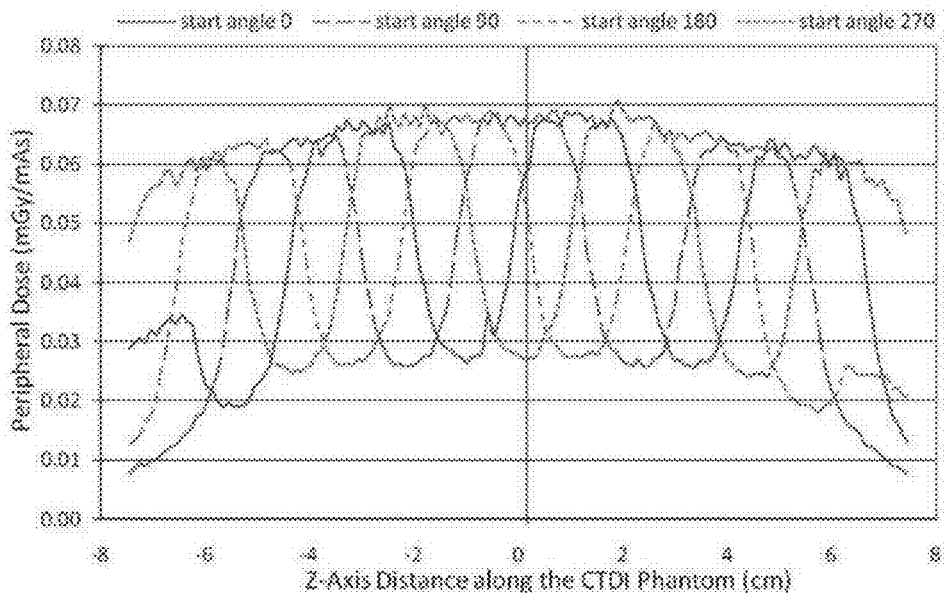
FIG. 3 illustrates the peripheral dose profile on a CTDI phantom for different tube start angles in accordance with some embodiments of the present invention.
FIG. 14 is a table of the maximum organ dose reduction for several pregnant female phantoms under different simulated pitch values and collimation settings in accordance with some embodiments of the present invention.

Since the radiation dose pattern is periodic, and nearly sinusoidal in some cases, there can also be a phase shift of this pattern. That is to say, the radiation dose pattern can be shifted along the longitudinal axis of the patient. This shift can be caused by a change in the starting angle of the helical pattern of the X-ray source. The results of this shift in X-ray source movement pattern are shown in FIG. 3, which illustrates the peripheral dose profile on a 32 cm CTDI phantom for different start tube start angles using a constant pitch of 1.5 and a measured beam width of 34.1 mm. Each pattern shows the same basic radiation dose periodic pattern, but just shifted along the z-axis (i.e., longitudinal axis) of the object.

Figure 4:
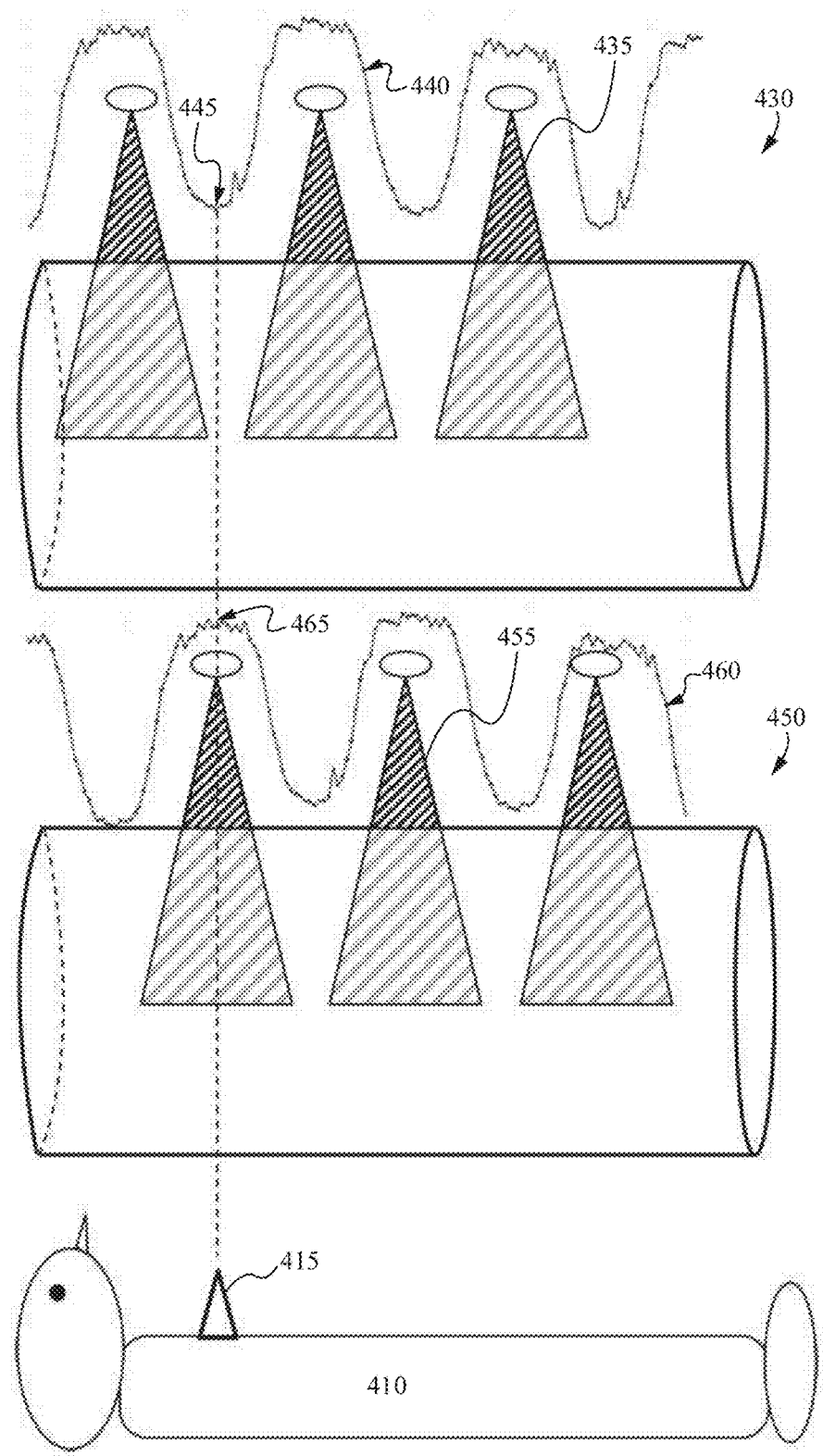
FIG. 4 illustrates the X-ray tube position and corresponding surface dose distribution for two different tube start angles in accordance with some embodiments of the present invention.

The present invention exploits the periodic sinusoidal behavior of the radiation dose to reduce the dose to a specific organ by varying the tube start angle, especially for a small peripheral organ on patients. FIG. 4 illustrates different tube positions and the corresponding surface dose distribution along the z-axis under two scenarios, 430 and 450, with different tube start angles at a pitch of 1.5. An illustrative patient 410 with breasts 415 on the surface is shown at the bottom as well. FIG. 4 shows that the dose to the breasts 415 of the patient 410 can be affected by selecting different tube start angles. In the upper scenario 430, divergent X-ray beams 435 from the tube create a radiation dose profile 440. The cold spot of the radiation dose 440 meets the location of the breasts at spot 445, resulting in the breasts 415 receiving a minimum dose. In the lower scenario 450, divergent X-ray beams 455 from the tube create a radiation dose profile 460. The hot spot of the radiation dose 460 meets the location of the breasts at spot 465, resulting in the breasts 415 receiving a maximum dose.

The method of the present invention, involving the reduction of the radiation dose to an organ by selecting a specific tube start angle, is particularly effective if the size of the organ is relatively small compared to the period of the dose variation curve. In developing the present invention, the inventors investigated the possibility of manipulating the tube start angle so that a small organ on a patient could receive a lower dose to that selected organ. In this investigation, they simulated CT scans under different conditions (pitch, collimation, etc.) for different patient models (infant, small child, adult female, and pregnant patient) to determine the organ dose reduction that results solely from altering the start angle of the X-ray source. These simulations and their results will be discussed in further detail below. The dose reduction should not have any effect on image quality, as there is no change in mAs or total mAs.

The present invention exploits the variation in radiation dose at the surface of the patient in such a way as to locate the minimum dose region at the location of a radiation sensitive organ. The method of the present invention is most effective when the organ in question is small with respect to the width of the X-ray beam (i.e., smaller than the actual radiation beam width) and located peripherally (organs located more along the patient's midline in depth, such as the midline of FIG. 2B, do not benefit as much from this variation in surface dose).

In some embodiments, the present invention involves first determining the location of the radiation sensitive organ of interest. Then, given information about the X-ray beam collimation setting, the table travel increment (or pitch), the location of the organ of interest, as well as the start location (table position) where the X-ray beam will first turn on, two things are then calculated. First, the number of rotations around the gantry that the X-ray tube will make before it reaches the organ of interest is calculated. Then, the start angle of the X-ray source can be calculated using the number of rotations so that the X-ray source will be positioned at the appropriate angle when it crosses the organ of interest. In some instances, the appropriate angle is opposite the organ of interest (i.e., the X-ray tube should pass over the location of the organ to the posterior of the patient when the organ lies anteriorly), and in other instances, the appropriate angle is directly over the organ of interest (i.e., the X-ray tube should pass anteriorly if the organ lies anteriorly). The desired angular position of the X-ray source as it passes over the organ of interest is primarily determined by the table travel or pitch of the scan, which is known before the scan is performed and, therefore, can be included in the calculations.

For each specific scan (with a fixed nominal beam collimation and pitch) on a specific patient, the relationship between the organ crossing tube angle (OCTA), which is the angle of the X-ray source as it crosses the longitudinal center of the organ being investigated, and the tube start angle can be calculated given the location of the organ. If the pitch is 1.5 (or generally greater than 1), the organ will receive a minimum dose when OCTA=180 degrees. Therefore, a corresponding tube start angle can be calculated and selected to be the optimal dose reduction angle. If the pitch is 0.75 (or generally less than 1), the organ will receive a minimum dose when OCTA=0 degrees. Therefore, a separate tube start angle can be calculated as the optimal dose reduction angle. When an optimal dose reduction tube start angle is selected, the organ will receive the lowest radiation dose from this specific scan.

Currently, manufacturers of CT scanners do not allow the user to control the start angle of the X-ray beam. In some scanners, it is essentially a continuous random variable, as any start angle is allowed. In others, only limited start angles are allowed, which is more of a discrete random variable. No manufacturer currently uses any control of the start angle for any radiation dose reduction in a helical scan.

In some embodiments, the present invention includes software with a graphical interface to provide the optimal tube start angle. In some embodiments, a topogram (also known as the planning radiograph) can be used before the CT scan in order to determine the location of the organ on the patient. Then, the location of the organ, the scan start location, the nominal beam collimation, and the pitch being used in that specific scan can be input into the software, which will calculate the optimal tube start angle.

When manufactures want to implement this dose reduction tool, the software can be embedded in their control station package, where the user only needs to specify the organ for which he/she wants the dose reduction. Then, the scan will be performed at the optimal tube start angle automatically and an estimated dose reduction percentage will be provided in a report.

The inventors of the present invention have found that the dose reduction using the invention can be quite large. For pediatric patients, the dose reduction to breast, testes, thyroid, and lens of eyes is considerable (20% to 40%). For adult patients, the dose reduction is considerable for the lens of eyes. For pregnant patients at early gestational stage (i.e, less than 10 weeks), the dose reduction to the fetus can be up to 17-18%. Additionally, the method of the present invention does not involve any change of mAs or kVp, and thus does not degrade image quality at all, whereas other methods, such as lowering mAs/kVp, can have some effect on image quality, although they do not affect the diagnostic outcome very much.

Furthermore, all current radiation dose reduction techniques are not specific to any radiation sensitive organ. The techniques described herein can reduce radiation dose to a specifically identified radiation sensitive organ.

The method of the present invention and its calculations have been developed and tested by simulations using a CT model, which was rigorously validated by physical measurements. The present invention includes software that provides the optimal tube start angle based on necessary inputs.

In currently available commercial CT scanners (e.g., Siemens, GE, Toshiba, Philips), the tube start angle is not controlled by the user. It is either a completely random variable (any start angle is possible) or a limited random variable (only certain start angles are allowed, but are still not controlled by the user). Therefore, the radiation dose received by some organs, especially small radiation-sensitive organs, can be quite different from patient to patient. The method of the present invention can reduce the cancer risk for pediatric patients and a developing fetus, which is high due to their higher organ radiosensitivity and longer lifetime. Additionally, it can also reduce the possibility of developing cataract for adult patients by reducing radiation dose to the lens of the eye. As the radiation from medical procedures, primarily from CT, continues to be a concern, the present invention would therefore be very attractive for new or existing commercial CT manufacturers.

As will be discussed in further detail below, the radiation doses to several radiosensitive organs (including breasts, thyroid, uterus, gonads, lens of eyes) from an MDCT scanner were estimated using Monte Carlo simulation methods on voxelized patient models, including GSF's Baby, Child, and Irene. The radiation dose to a fetus was also estimated using pregnant female models. Whole body scans were simulated using 120 kVp, 300 mAs, both 28.8 mm and 40 mm nominal collimation, and pitch values of 1.5, 1.0 and 0.75 under a wide range of start angles (0 to 340 degrees in 20 degree increments). The relationship between tube start angle and organ dose was examined for each organ and the potential dose reduction was calculated.

Some organs demonstrated strong dose variation depending on the tube start angle. For small peripheral organs (e.g., the lens of eyes on Baby phantom at pitch 1.5 with 40 mm collimation), the minimum dose can be 41% lower than the maximum dose, depending on the tube start angle. In general, larger dose reduction occurs at wider collimation for smaller, peripheral organs in smaller patients. A pitch of 1.5 and a pitch of 0.75 have different mechanisms of dose reduction. For pitch 1.5 scans, the dose is usually lowest when the tube start angle is such that the X-ray tube is posterior to the patient when it passes the longitudinal location of the organ. For pitch 0.75 scans, the dose is lowest when the tube start angle is such that the X-ray tube is anterior to the patient when it passes the longitudinal location of the organ.

It has been found that helical MDCT scanning results in "cold spots" (pitch 1.5) and "hot spots" (pitch 0.75) that are created both at surface and even in-depth locations within patients. If organs have a relatively small longitudinal extent, their dose can be reduced by selecting the tube start angle such that the location of these spots can be manipulated by appropriately selecting the tube start angle.

The Monte Carlo method has been used to simulate radiation dose deposition from CT in several previous efforts. For the work of the present invention, a Monte Carlo particle transport package, MCNP eXtended v2.6 (MCNPX), which was developed at Los Alamos National Laboratory, was utilized to perform the simulations. The simulations were operated in photon transport mode with a low-energy cutoff of 1 keV. Charged-particle equilibrium (CPE) was assumed so that all the secondary electrons deposit their energy at the photon interaction sites. A 64-slice CT scanner system (Sensation 64, Siemens Medical Solutions, Forcheim, Germany) was modeled for all simulations using Monte Carlo-based methods. The widest available beam collimation of this scanner is 24×1.2 mm, which yields a nominal beam width of 28.8 mm. The corresponding actual beam width is 32.2 mm in air at the isocenter, which was evaluated from the measured radiation profile using Optically Stimulated Luminescence doismeteres (OSLs, CT Dosimeter, Landauer, Inc. Glenwood, Ill.). The source file of MCNPX 2.6 was modified to model a Siemens Sensation 64 scanner such that helical scans with any clinically relevant kVp, mAs, pitch values, and collimation settings could be simulated.

The helical pathway of the CT source in x, y, z were explicitly defined for any scan given the pitch, table feed, tube start angle, nominal collimation, and scan start and stop location. The location of each emitting photon was then sampled from the pathway specified. The photon spectra for a 120 kVp source and descriptions of any beam filtration, including the bowtie filter, as well as the geometry were provided by the manufacturer. This model was validated and benchmarked using comparisons based on standard dosimetry (CTDI) measurements and corresponding simulations, which were in agreement to within 5%.

Several different patient models were evaluated and are described below. They are the Baby, Child, and Irene models from the GSF (now Helmholtz Zentrum München) family of computational, voxelized models (N. Petoussi-Henss, M. Zankl, U. Fill and D. Regulla, "The GSF family of voxel phantoms," Physics in Medicine and Biology, 89 (2002) and M. Zankl, U. Fill, N. Petoussi-Henss and D. Regulla, "Organ dose conversion coefficients for external photon irradiation of male and female voxel models," Physics in Medicine and Biology, 2367 (2002)), as well as a limited sample of pregnant patient models described in Angel et al. ("Radiation Dose to the Fetus for Pregnant Patients Undergoing Multidetector CT Imaging: Monte Carlo Simulations Estimating Fetal Dose for a Range of Gestational Age and Patient Size," Radiology 249, 220-227 (2008)). In order to incorporate each phantom into Monte Carlo code for particle transportation calculation, the element composition and mass density of each organ is required. These values were derived from the ICRU 44 organ composition tables (ICRU, "Tissue Substitutes in Radiation Dosimetry and Measurement," ICRU Report No. 44 (1989)). For the GSF models, this included all radiosensitive organs, though only six were explicitly studied. For the pregnant patient models, only the uterus, gestational sac, and fetus were explicitly studied. All other voxels were assigned to one of six tissue categories (air, lung, fat, water, muscle, or bone) based on Hounsfield Unit as described by DeMarco et al. ("A CT-based Monte Carlo simulation tool for dosimetry planning and analysis," Medical Physics 25, 1-11 (1998)).

The GSF phantoms are a series of voxelized phantoms with segmented individual organs. Baby, Child and Irene were selected from the GSF family to represent small patients with different body habitus. Some basic parameters of these three models are summarized in Table I of FIG. 11. The selected organs used for evaluating dose variation were the testes, ovaries, breasts, thyroid, uterus, and eye lenses, when available in the phantom. These organs were selected because they are all relatively small in size, and so a higher dose reduction is expected for these small organs. It should be noted that although Baby and Child are female phantoms, testes were added into the gonads by GSF in order to calculate average gonads doses. Also, despite the fact that Child is a female phantom, no breast voxels were identified.

In addition to the GSF whole body phantoms with various age and size, a series of previously developed pregnant female models with various gestational stages were used to investigate the dose to the fetus. The CT images of pregnant females were gathered from CT examinations of pregnant patients performed under clinically indicated scans, such as trauma. The uterus, gestational sac, and fetus from these CT images were contoured by radiologists whenever they were visible. These three types of tissues were assigned as separate individual organs in the phantom and they were selected to evaluate the dose variation caused by the tube start angle in CT scans. In total, there were 24 pregnant female models in this series of phantoms, from which 4 of them were selected for to represent different gestational stages, with emphasis on the early gestational stages because the size of the fetus is smaller. These 4 models are referred to as F26, F10, F7, and F31. The fetal age, size of the uterus in longitudinal direction, and the studied regions for each model are summarized in Table II of FIG. 12. The uterine length in the longitudinal direction for each model was estimated from the original voxel data.

Under CPE conditions, the absorbed dose to each voxel is equivalent to the collision kerma in the voxel, which was calculated by multiplying the mass energy-absorption coefficients with the energy fluence evaluated by MCNPX based on track-length estimation. Then, the mean dose to an organ was estimated by averaging the dose to each voxel across all the voxels belonging to the organ. All the organ dose results were converted from MCNPX raw output to absolute dose normalized to tube current (in mGy/100 mAs) using normalization factors calculated from scan measurements in air and corresponding simulations in air.

For all the experiments, simulated whole-body scans were performed for each phantom using 120 kVp and 300 mAs. In this disclosure, "whole-body scan" refers to the full coverage of all the voxels in every phantom. For GSF phantoms, the scan limits extend from the top of the head to the end of the feet. For pregnant patient models, they extend from the lower thorax to the pubic symphysis.

To investigate the dose variation from different tube start angles, various tube start angles ranging from 0 degrees to 340 degrees with an interval of 20 degrees were used for each set of simulations, which means 18 simulations were performed on each patient model using different tube start angles, while keeping all the other scanning parameters constant. In the simulations, 0 degrees means that the tube is at the top of the gantry (i.e., the 12 o'clock position). To make the results more intuitive, the angle that is reported is not the start angle, but rather the angle of the X-ray source as it crosses the longitudinal center of the organ being investigated, which is referred to as the "organ crossing tube angle" (OCTA). For example, for the Baby GSF phantom, when using a pitch of 1.5 and a nominal beam collimation of 28.8 mm, a start angle of 0 degrees (i.e., the angle of the source is at 12:00 position at the start of the X-ray beam being on), the angle of the X-ray source as it crosses over the center of the eye lens is 107 degrees (OCTA=107 degrees). When the OCTA that results in the minimum dose for a particular organ is known, then the appropriate start angle can be calculated, as will be described below.

To explore the correlation between the magnitude of organ dose reduction and the scanning parameters, pitch and collimation values were varied for each set of patient models. For the GSF models, three clinically relevant pitch values of 0.75, 1, and 1.5 were tested. For the pregnant patient models, only the pitch values of 0.75 and 1.5 were tested. For all patient models, two sets of collimation settings were simulated: one is the nominal beam width of 28 mm with the actual beam width of 32.2 mm, and the other one is a case where the nominal beam width is 40 mm and the actual beam width is 44.7 mm, calculated based on the ratio of the actual/nominal beam width for the 24×1.2 mm collimation. While a 40 mm beam width is not currently available in the modeled scanner, many other manufactures have scanners with the same or even larger beam widths.

For each patient model, organ of interest, and set of scanning parameters (pitch and nominal collimation pair), the OCTA that results in the highest dose is used as the worst case reference. Based on this worst case reference value, the dose reduction from the worst case is calculated for each OCTA value. This value demonstrates how much savings is possible compared to the worst case OCTA. In currently available MDCT scanners, there is no specific ability to control the start angle. Therefore, the OCTA is similar to a random variable, with some patients receiving the highest dose to a specific organ and some patients receiving the lowest dose to that same organ. For each experiment discussed below, all results are presented as dose reduction compared to the worst case.

MATLAB subroutines were created to compute the OCTA at a given tube start angle, as well as to obtain the location, size, and centroid for each organ in each patient model. Given an organ's location and size information, the centroid along the longitudinal (z) axis is determined by averaging the longitudinal location of all the voxels assigned to the organ. When that centroid location is known, as well as the scan start location (start of X-ray beam on) and the table feed per rotation (the product of pitch and nominal beam collimation), then the number of gantry rotations that will occur from the scan start location to the centroid of the organ can be obtained by using the following equation:

$$R=(OLoc-SLoc)/(pitch \times N),$$

where R is the number of rotations of the tube from the scan start location to the location of the center of the organ, OLoc is the location of the organ centroid along the longitudinal axis (z-axis), SLoc is the longitudinal axis scan start location (where the X-ray beam first turns on), N is the nominal beam collimation, and pitch is conventionally defined. It is noted that pitch×N=table feed in mm/rotation. Then, the OCTA can be obtained by using the following equation:

$$OCTA=\text{tube start angle}+(360\times(R-\text{floor}(R))),$$

where floor(R) is the integer part of R. Accordingly, the tube start angle can be obtained using the following equation:

$$\text{tube start angle}=OCTA-(360\times(R-\text{floor}(R))).$$

In some embodiments, the location of the center of the organ is obtained by averaging the longitudinal location of all the voxels assigned to the organ. This location is actually the longitudinal location of the organ centroid. The MATLAB subroutine reads in all the voxel data for each phantom and performs the calculations shown above. It is noted that the tube start angle that yields a particular value of OCTA for each organ is patient specific and organ specific. For example, an OCTA of 180 degrees for the lens of the eye can have a different start angle from the one required to yield an OCTA of 180 degrees for the thyroid. Similarly, an OCTA of 180 degrees for the lens of the eyes can correspond to different start angles for the Baby phantom and for the Child phantom.

Figure 5A:
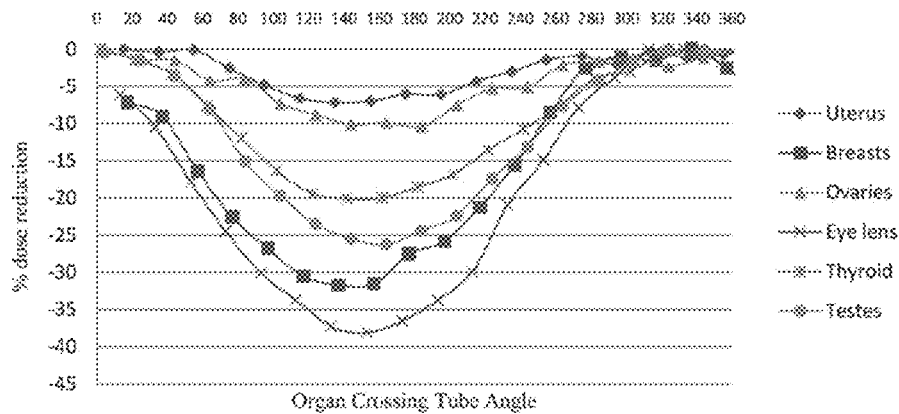
FIGS. 5A-F illustrate dose reduction curves for different organs in a baby phantom using different pitch and collimation values in accordance with some embodiments of the present invention.
Figure 5B:
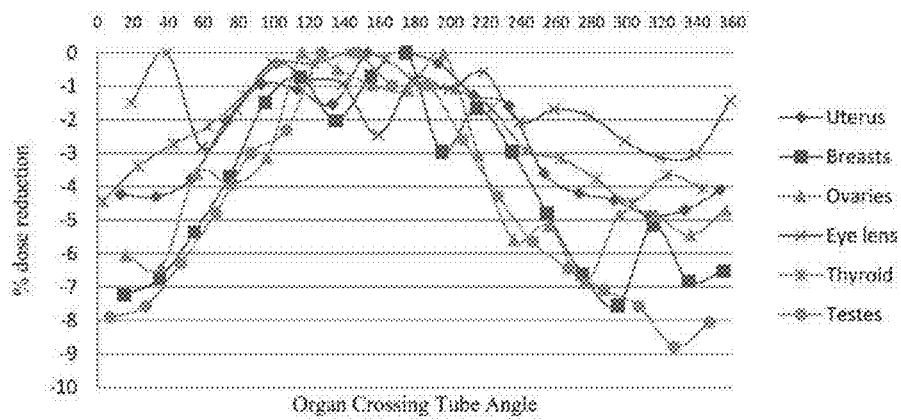
Figure 5C:
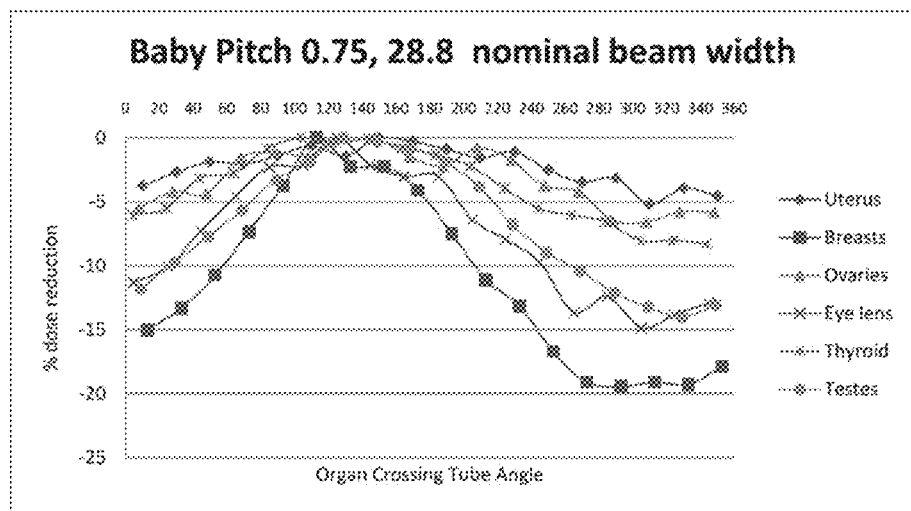
Figure 5D:
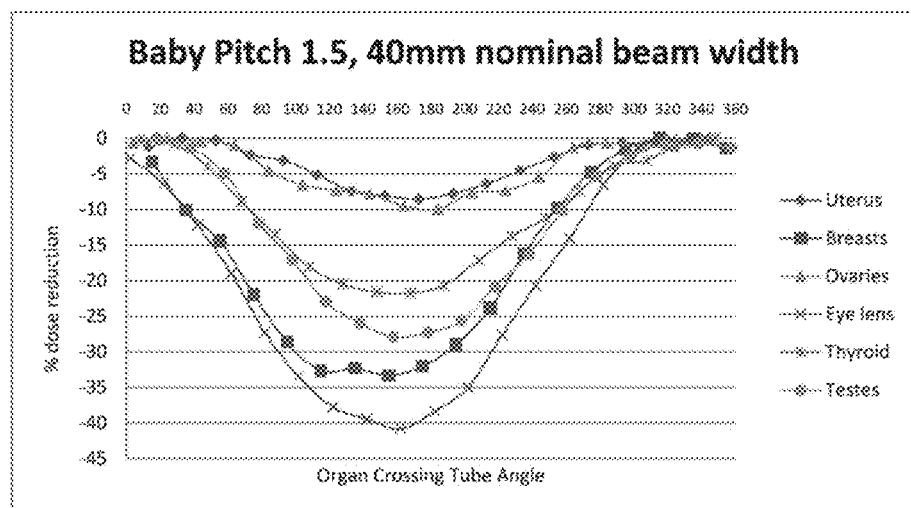
Figure 5E:
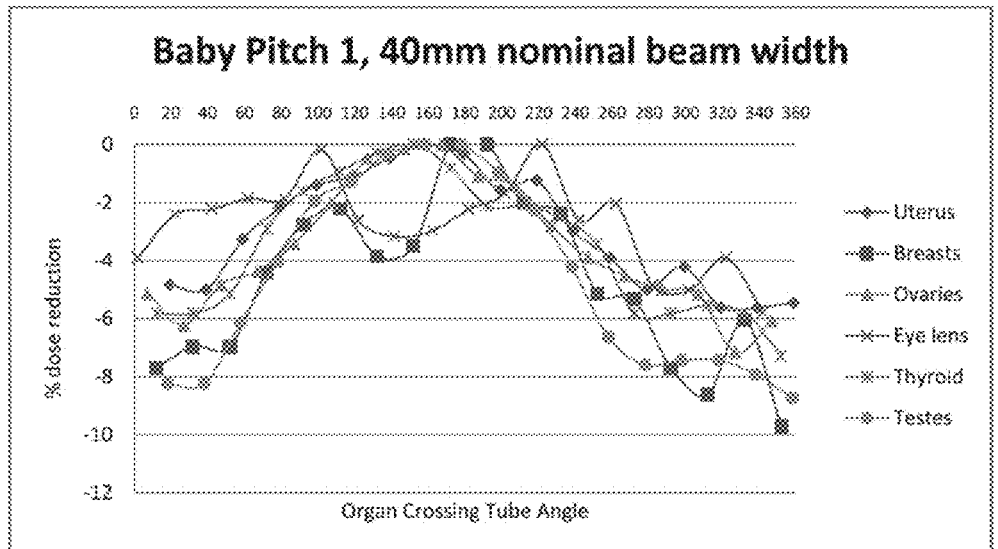
Figure 5F:
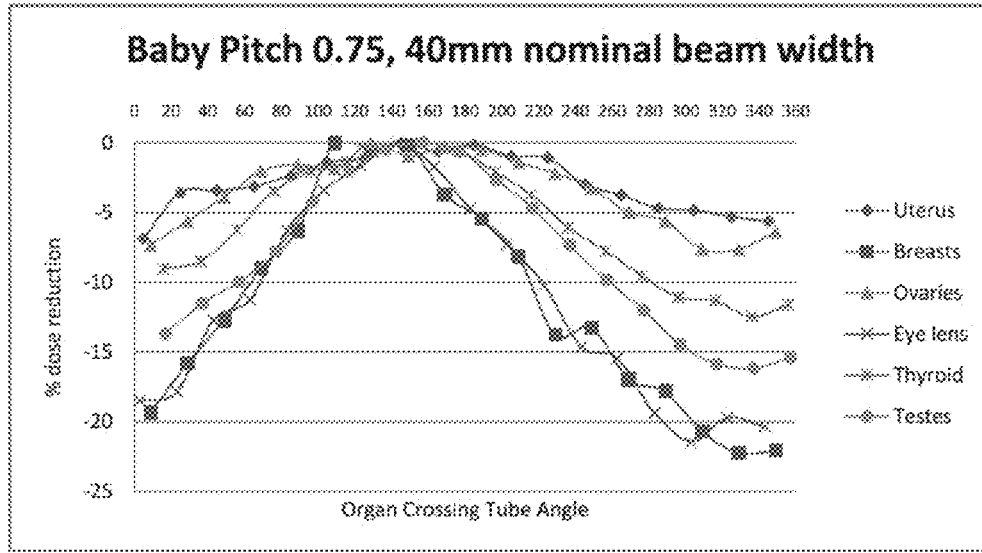

For each patient model, organ, pitch and collimation combination, a set of 18 simulations were performed, each with different tube start angles. The organ dose reductions (compared to the worst case OCTA) can be presented graphically by plotting the percent reduction of organ dose (on the y-axis) as a function of the OCTA (on the x-axis). Since three pitch values (0.75, 1, 1.5) and two collimation settings (28.8 mm, 40 mm) were simulated, there are six such graphs possible for each patient model. As an example, the dose reduction curves for all the studied organs in Baby phantom with all pitch values and nominal collimations are shown in FIGS. 5A-F, with each figure demonstrating a different pitch/collimation combination. The organ dose reduction as a function of OCTA can be observed from these figures. For example, as shown in FIG. 5D, the dose reduction compared to the worst case scenario for breasts for a scan with 1.5 pitch and 40 mm nominal beam width is almost 35%. For a testes dose from the same scan, the difference is 28%. It is noted that the magnitude of dose variation is caused by solely changing the tube start angle, while keeping all the other scan parameters constant.

These results indicate that for Baby, the largest dose reductions occur for eye lens, thyroid, breasts and testes—all of which are at or near the surface of the patient and all of which have at least 20% dose reduction for a pitch of 1.5. These results also show that the largest dose reductions occur for a pitch of 1.5 and a pitch of 0.75. A pitch of 1 does not show large dose reductions at all, regardless of the OCTA. This is not surprising because the magnitudes of the surface dose variations are much smaller when using a pitch of 1.0 than with a pitch of 1.5 or a pitch of 0.75. These figures also show that the OCTA is different for different pitch values. It is approximately 180 degrees for a pitch of 1.5 and approximately 0 degrees for a pitch of 0.75. Finally, they also show a slightly larger dose reduction for a wider beam collimation setting (40 mm compared to 28.8 mm).

Similar figures of organ dose reduction as a function of OCTA could be made for Child and Irene patient models. The behavior is similar and so they are not shown here. Rather, the organ dose reductions for each patient model are summarized in Table III of FIG. 13 for all three GSF phantoms.

It can be shown from Table III that for the adult patient model (Irene), the dose reduction is not quite as large as the pediatric models, except for the lens of the eyes. But for the pediatric models (Child and Baby), the dose reduction to the breast, testes, thyroid, and eye lenses are all considerable (on the magnitude of 20% or more). Ovaries and uterus on pediatric patients have lower dose reduction (on the magnitude of 10%), because these two organs are located at a greater depth (rather than at the surface) than the other four organs.

By comparing the results across different pitch values (different columns in Table III), it can be seen that the magnitude of dose reduction for a pitch of 1.5 is the largest, with the dose reduction up to 54% for Irene's eye lens at 40 mm nominal beam width. For a pitch of 0.75, the magnitude of dose reduction is not as high as that for a pitch of 1.5, but it is still considerable, for example, 23% for Child's eye lens at 40 mm nominal beam width. The dose reduction is not large for a pitch of 1, where it is below 10% for most of the organs in all GSF models.

By comparing the results across different collimations (28.8 mm and 40 mm in Table III), it can be seen that the magnitude of dose reduction for 40 mm nominal beam width is slightly larger than that for 28.8 mm nominal beam width for almost all of the cases. For example, for Child's testes, the maximum dose reduction values at 28.8 mm nominal beam width for a pitch of 1.5, a pitch of 1.0, and a pitch of 0.75 are 33%, 6%, and 11%, respectively, while at 40 mm nominal beam width they are 36%, 9%, and 16%, respectively.

Figure 6:
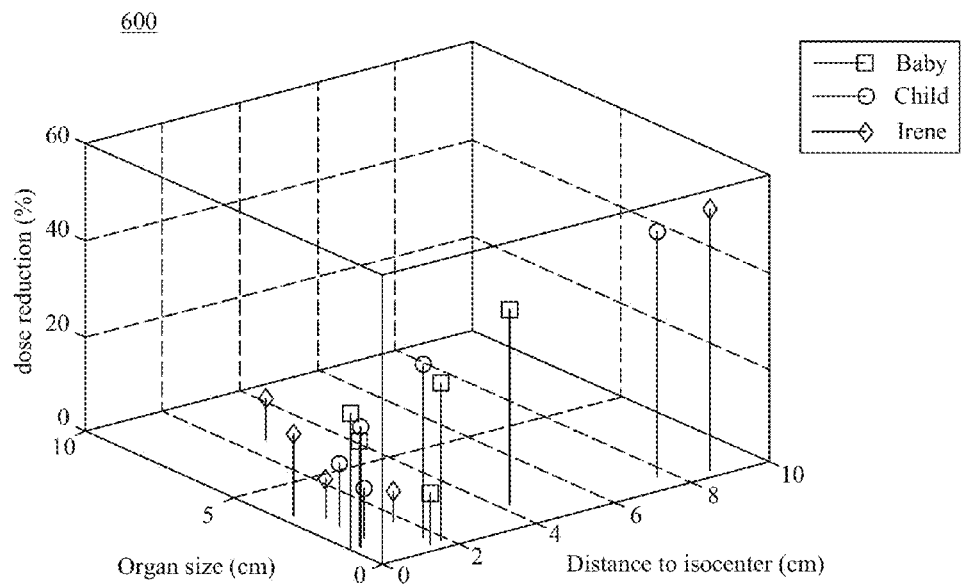
FIG. 6 illustrates the dose reduction for individual organs of three different phantoms in accordance with some embodiments of the present invention.

The comparison of the results across different organs on different patient models (different rows in Table III) is not as straightforward. In general, larger dose reduction occurs for smaller, peripheral organs in smaller patients. For example, the maximum dose reduction values of the eye lenses for all three phantoms are relatively large because the eye lens is a small surface organ. The maximum dose reduction for 40 mm collimation at a pitch of 1.5 (the fourth column in Table III) was plotted in a three-dimensional space as a function of both organ length in the longitudinal dimension and the distance from the center of the organ to the isocenter in AP dimension, which is shown in FIG. 6. From FIG. 6, it can be observed that there is a general trend: as the organ size decreases and the distance to the isocenter increases, the dose reduction will increase.

Figure 7A:
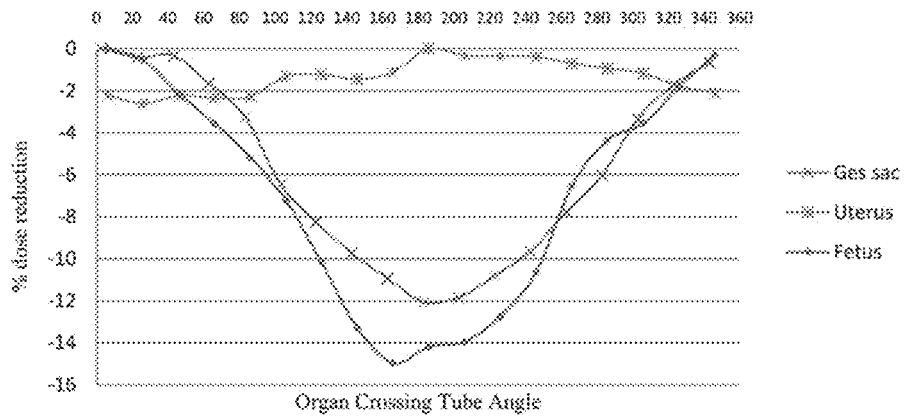
FIGS. 7A-B illustrate the dose reduction curves for different pitch values as a function of the organ crossing tube angle in accordance with some embodiments of the present invention.
Figure 7B:
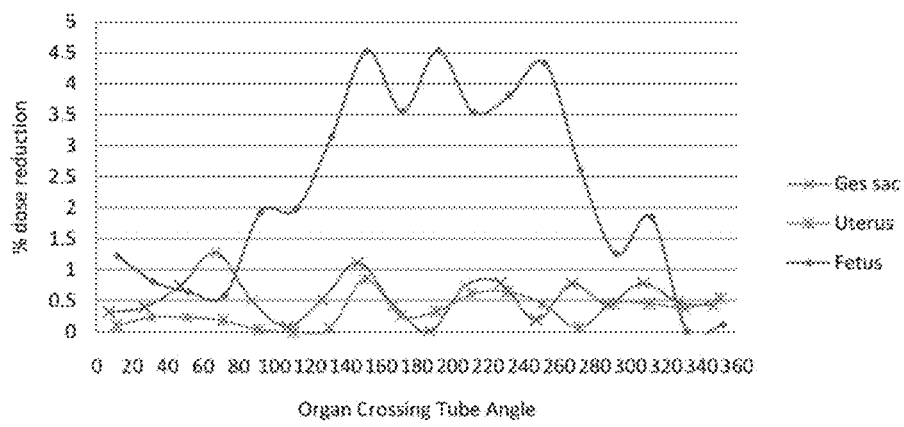

The organ dose variation curves for pregnant female models were plotted in the same way as for GSF phantoms. The organ dose variation can again be clearly observed. As an example, the percent dose reduction curve as a function of OCTA from a simulated scan with 40 mm nominal collimation, and pitches of 1.5 and 0.75 for F7 phantom are shown in FIG. 7A and FIG. 7B, respectively.

The maximum dose reduction for organs from the combinations of all the pitch and collimation settings is shown in Table IV of FIG. 14. This table shows that the magnitude of dose reduction to the fetus can exceed 10% for the early gestational age models (12 weeks) for a pitch of 1.5 and a 28.8 mm collimation setting, and increases to approximately 17-18% for a 40 mm collimation setting. Results from a pitch of 0.75 yield smaller dose reductions with only the earliest gestational age model yielding an 8% dose reduction for the 40 mm collimation setting. Results from the later gestational model (19 weeks) used show very small dose reduction regardless of pitch, collimation, or start angle, which is to be expected for larger objects or organs.

This table also indicates that dose reductions are not as large as those observed in Baby and Child phantoms. This is understandable because the early gestational age fetus, while small, is located somewhat centrally in the body. This table shows some similar general trends between the dose reduction and length in longitudinal dimension as in the GSF models in that a smaller size fetus has higher dose reductions. For example, at a pitch of 1.5, the maximum dose reduction is above 10% for F24, F10, and F7. But for the pregnant patient model with a later gestational age (19 weeks), the fetus is larger and the dose reduction is nearly negligible (F31). These results are also similar to that for GSF phantoms in terms of pitch and collimations: a pitch of 1.5 and a wider collimation yield larger organ dose reductions.

It should be noted that for the two phantoms with the earliest gestational age (F24 and F10), dose to the fetus was not directly simulated because the fetus tissue was too small to be identified by the radiologists from CT images. Originally, the radiologist identified the gestational sac and the inventors estimated the dose to that tissue to serve as an indirect estimate of the dose to the fetus. This does not mean that there is no fetus dose. In fact, they can have a very high magnitude of dose variation from varying the tube start angle because of their small size. Furthermore, the development of the fetus is very active in the initial few weeks, so they are even more sensitive to radiation.

The computational time for each MCNPX simulation (fixed pitch, collimation, and tube start angle) was about 5 minutes on a parallel computing cluster server with 64 AMD 2.0 GHz processors. Because the requirement of the relative errors of the output results was very high, a total of 100 million photon histories were used for each simulation. The standard deviation of all the results from MCNPX was within 1.2%, with most of them below 0.5%. The scenarios where the error is higher than 0.5% happen when the size of the organ is very small (e.g., lenses of eyes), because, for such cases, the number of photons that enter the organ can be small.

Simulation results demonstrate a range of dose reduction for various organs in various phantoms undergoing a full body scan. This dose reduction can be large. For example, for Baby phantom, the maximum reduction of the breast dose could be as high as 33%. For pediatric patients, the dose reduction to breast, testes, thyroid, and eye lenses is considerable (20% or more), while the dose reduction to ovaries and uterus is lower (10%). For adult patients, the dose reduction is only considerable for the eye lenses. For pregnant patients at an early gestational stage (<10 weeks), the dose reduction to the fetus can be up to 17-18%.

The magnitude of organ dose reduction resulting from varying tube start angle is highly related to the location of the organ, size of the organ, and anatomy in the vicinity of the organ in question. If the organ is perfectly at the isocenter, the organ would have very minor dose variation from varying tube start angle because the dose distribution at isocenter is nearly uniform. If the organ is relatively large, such as the lung or liver, it also will not have significant variation because its dimension in longitudinal direction is much larger than the period of the dose distribution (which is basically table feed per rotation), and the organ dose integrated over several periods will not be able to reflect the peaks and the valleys. For example, the organ dose of F31 pregnant patient phantom does not have considerable variations depending on the tube start angles because the organ (fetus) is relatively large. The anatomy in the vicinity of the organ in question is also an important factor. For example, the eye lens is surrounded by more bone than the breasts, so it has a higher magnitude of dose variation. In addition, although the fetus is almost at the isocenter, it can be surrounded and protected from radiation by the pelvis, except for the anterior direction. This will also result in some dose variation as a function of tube angle.

Since the table feed per rotation is the product of pitch and nominal collimation, these two parameters determine how 'continuous' the surface (or peripheral position) is covered by the primary beam. For example, if the table feed per rotation is much larger than the actual beam width (as with a pitch larger than 1.0), there can be considerable area on the surface that is not covered by the primary beam and, hence, the longitudinal dose distribution will have a higher variation. So theoretically, as the pitch and nominal collimation increase, the organ dose would have a larger dose reduction. This was illustrated in Table III, where the maximum dose reduction is higher for a pitch of 1.5 than that for a pitch of 1 for all cases, and it is higher for a 40 mm nominal beam width than that for a 28.8 mm nominal beam width.

Figure 8:
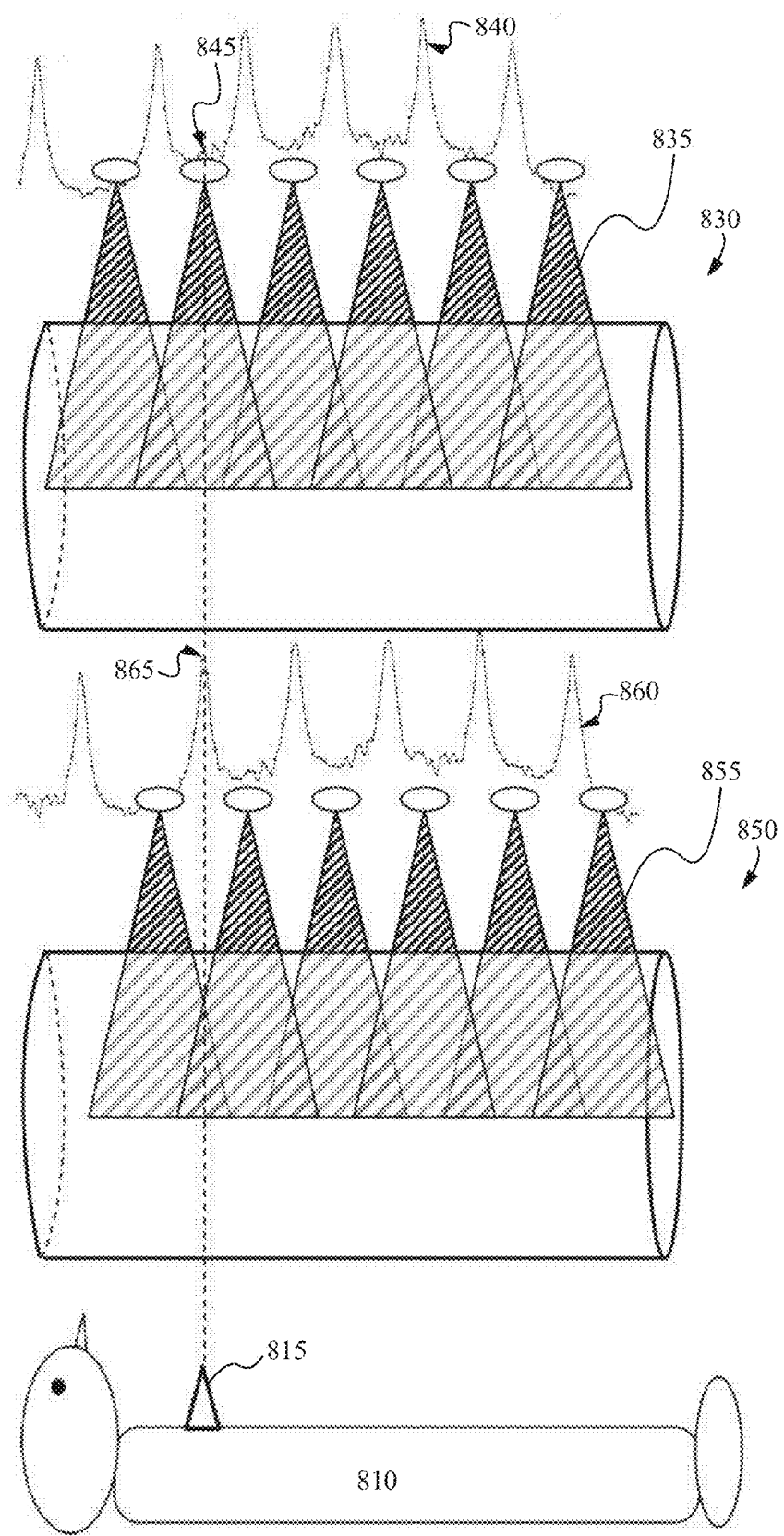
FIG. 8 illustrates the X-ray tube position and corresponding surface dose distribution for two different tube start angles in accordance with some embodiments of the present invention.

However, the dose reduction of a pitch of 1 is not higher than that for a pitch of 0.75. This is because as the pitch decreases to a certain value, the overlap of the adjacent radiation beams occurs, resulting in an overlap peak. As illustrated in FIG. 8, this scenario creates a new mechanism of organ dose variation, where inside the overlap region the organ receives a higher dose and outside the overlap region the organ receives a lower dose. Therefore, there is a "threshold" pitch for each organ in each phantom, such that the larger the difference between the pitch used in the scan and the threshold pitch is, the higher the achievable dose reduction could be. It is expressed in the following equation:

$$P_{threshold} = (1 - d/\text{iso}) \times (A/N),$$

Where d is the distance between the center of the organ to the isocenter in the A-P dimension, A is the actual beam width, N is the nominal beam width, and iso is the distance between the X-ray tube anode to the isocenter. Typically d (less than 10 cm for most of the organs) is much smaller than iso (usually 50 cm to 60 cm), so the threshold pitch can be approximated by A/N, which is about 1.1 here.

FIG. 8 is a diagram illustrating different tube positions and the corresponding surface dose distribution along the z-axis under two scenarios, 830 and 850, with different tube start angles at a pitch of 0.75. An illustrative patient 810 with breasts 815 on the surface is shown at the bottom as well. FIG. 8 shows that the dose to the breasts 815 of the patient 810 can be affected by selecting different tube start angles. In the upper scenario 830, divergent X-ray beams 835 from the tube create a radiation dose profile 840. The radiation dose 840 meets the location of the breasts at spot 845. In the lower scenario 850, divergent X-ray beams 855 from the tube create a radiation dose profile 860. The radiation dose 860 meets the location of the breasts at spot 865.

When the pitch used in the scan is higher than the threshold pitch, "cold spots" are created along the longitudinal direction of the organ (as illustrated in FIG. 4). In comparison, when the pitch used in the scan is lower than the threshold pitch, then overlap peaks result and "hot spots" are created as demonstrated in FIG. 8. If an organ has a relatively small extent in the longitudinal direction, its dose can be affected by these hot or cold spots, the location of which can be manipulated by selecting the tube start angle. Thus, two organ dose reduction strategies can be applied for these two different scenarios. For the first scenario (pitch $P > P_{threshold}$), the dose to an organ in question can be minimized if the tube start angle is selected in such a way that when the tube passes the organ, it is at the posterior side of the patient, which is opposed to the side of the studied organ. This corresponds to an OCTA of 180 degrees. For the second scenario (pitch $P < P_{threshold}$), the organ dose can be minimized by selecting a tube start angle such that when the tube passes the organ, it is at the anterior side of the patient which is the same side as the side of the organ. This corresponds to an OCTA of 0 degrees. Of course, the effectiveness of both techniques also depends on the anatomy in the vicinity of the organ in question. From FIGS. 5A-F, it is seen that the optimal angles are slightly off by about 20 degrees. One reason for this could be that the Baby model used is in a supine position slightly rolled to the left.

As the cone angle increases, the area of these cold or hot spots will also increase for helical scans, which causes a larger variation of organ dose depending on the tube start angle. Since very wide nominal beam width (>40 mm) MDCT scan systems are being introduced, this method can serve as an important dose reduction technique.

Figure 9A:
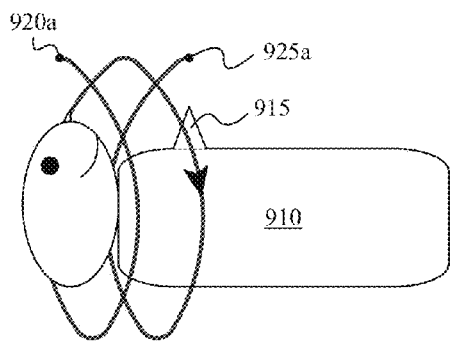
FIGS. 9A-B illustrate the different organ crossing tube angles for different tube start angles in accordance with some embodiments of the present invention.
Figure 9B:
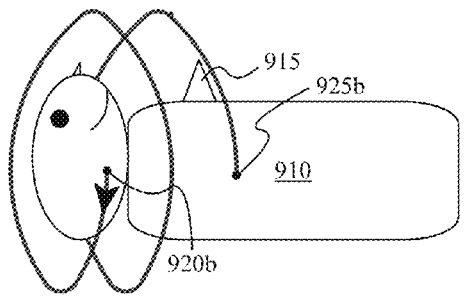

FIGS. 9A-B illustrate the difference in the OCTA when using different tube start angles. In FIG. 9A, a helical CT scan is performed on a patient 910 having breasts 915. The scan begins at point 920a, where the tube start angle is 0 degrees (i.e., at the 12 o'clock position centered over the head of the patient 910). The X-ray source moves in a helical pattern around the patient 910, as reflected by the arrow, and eventually crosses the patient's breasts 915 at point 925a with an OCTA of 0 degrees. In contrast, FIG. 9B shows a helical CT scan being performed on the patient 910 where the scan begins at point 920b with a tube start angle of 90 degrees (i.e., at the side of the head of the patient 910). The X-ray source moves in a helical pattern around the patient 910, as reflected by the arrow, and eventually crosses the patient's breasts 915 at point 925b with an OCTA of 90 degrees. It is noted that the path of the X-ray source in FIGS. 9A-B is shown using a perspective view in order to help show the helical pattern of the scan.

Figure 10:
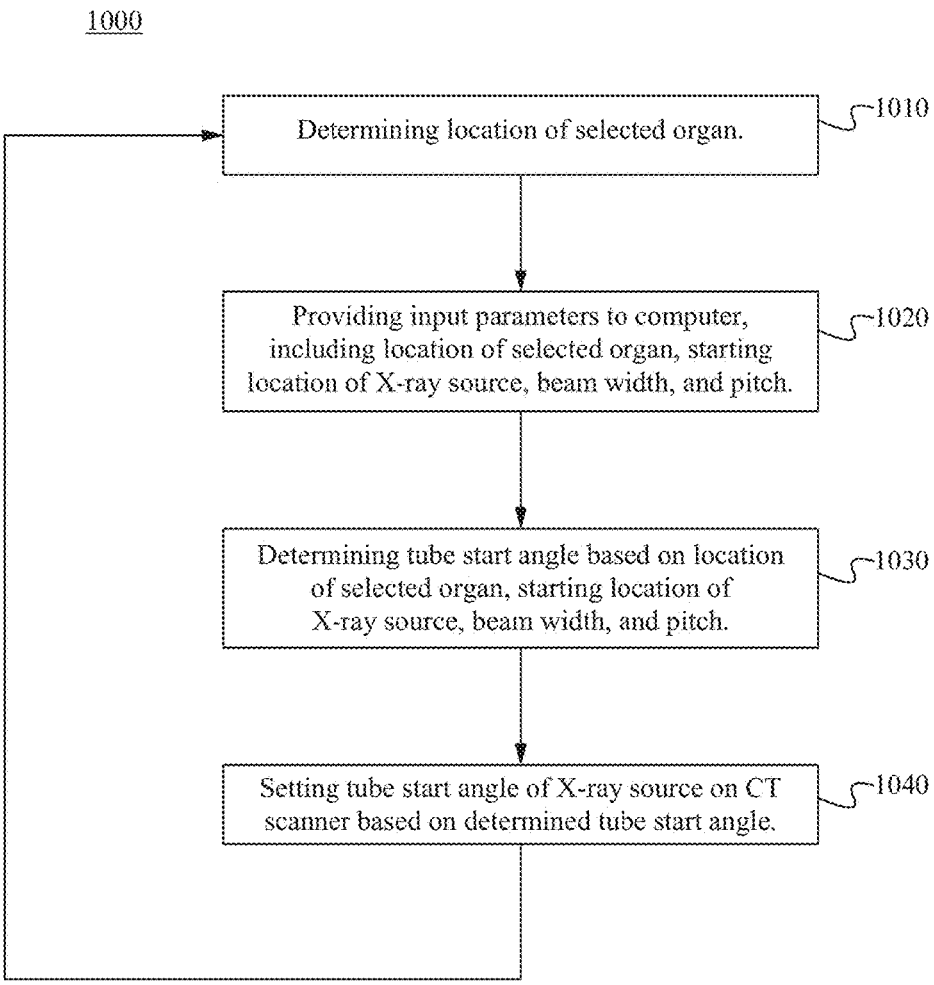
FIG. 10 is a flowchart illustrating a method of reducing radiation dose for a selected organ on a patient in a computed tomography (CT) scan in accordance with some embodiments of the present invention.

FIG. 10 is a flowchart illustrating a method 1000 of reducing radiation dose for a selected organ on a patient in a computed tomography (CT) scan in accordance with some embodiments of the present invention.

At step 1010, the location of the selected organ is determined. In some embodiments, the location of the selected organ is determined using a planning radiograph of the patient.

At step 1020, input parameters are provided to a computer that is configured to perform the core operations of the present invention. In preferred embodiments, the input parameters include the location of the selected organ, the starting location of the X-ray source being used in the CT scan, the beam width being used in the CT scan, and the pitch of the CT scan. In some embodiments, a user enters the input parameters using a graphical interface. However, it is contemplated that other means can be employed. In a preferred embodiment, the input parameters are provided as number values so that they can be used in calculations.

At step 1030, the computer determines the tube start angle for the CT scan based on the location of the selected organ, the starting location of the X-ray source being used in the CT scan, the beam width being used in the CT scan, and the pitch of the CT scan. It is contemplated that the tube start angle can be determined in a variety of different ways. However, preferably, the computer determines the number of tube rotations from the input parameters, and then determines the tube start angle using the determined number of tube rotations. In some embodiments, the number of tube rotations is determined using the equation:

$$R=(OLoc-SLoc)/(pitch \times N),$$

wherein R is the number of tube rotations from the starting location of the X-ray source to the location of the selected organ, OLoc is the location of the selected organ centroid along a longitudinal axis, SLoc is the starting location of the X-ray source along a longitudinal axis, pitch is the pitch of the CT scan, and N is the beam width of the CT scan. In some embodiments, the tube start angle is determined using the equation:

$$TSA=OCTA-(360 \times (R-\text{floor}(R))),$$

wherein TSA is the tube start angle, OCTA is the angle of the X-ray source of the CT scan as it crosses the longitudinal center of the selected organ, R is the number of tube rotations from the starting location of the X-ray source to the location of the selected organ, and floor(R) is the integer part of R.

At step 1040, the starting angle of the X-ray source on a CT scanner is set based on the determined tube start angle. In some embodiments, the computer automatically sets the starting angle on the CT scanner to the determined tube start angle. In some embodiments, a technician sets the starting angle on the CT scanner to the determined tube start angle. An X-ray scan can then be performed. The method can then be repeated for a different organ and/or patient.

Most of the investigated organs discussed in this disclosure are relatively small in size and easy to be anatomically located (e.g., lymph nodes are hard to be located). These organs happen to be located close to the anterior surface of the patient body. The dose reduction strategies would have been different if these small organs were located at the back or at the side of the body.

In some embodiments, the method of the present invention requires the knowledge of the location of the organ prior to the CT scan, which could be available from a scan projection radiograph or planning view. The localization of the organ position should be very accurate. In a preferred embodiment, the organ does not move during the examination.

The method of controlling the tube start angle to reduce the magnitude of organ dose offers a technique to reduce the dose to certain organ without compromising the image quality. This technique can be applied to a small organ on small patients, a fetus on pregnant patients with early gestational stage, or eye lenses on adult patients. Since tube current modulation (TCM) techniques do not perform very well for pediatric patients (e.g., because they are more circular than elliptical), this method can also serve as a complementary approach to TCM.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications can be made in the embodiment chosen for illustration without departing from the spirit and scope of the invention as defined by the claims.

What is claimed is:

1. A method of reducing radiation dose for a selected organ on a patient in a computed tomography (CT) scan that uses an X-ray source that rotates around the patient as the patient is lying down on a patient bed being translated along a longitudinal axis through an X-ray gantry to scan the patient, the method comprising:
   providing a computer associated with the CT scan;
   determining a tube start angle relative to a direction of the patient lying down on the patient bed for the X-ray source of the CT scan, via the computer, based on a location of the selected organ along the longitudinal axis, a starting location of the X-ray source along the longitudinal axis, a beam width of the CT scan, and a pitch of the CT scan, wherein the tube start angle is defined by (i) a line between the X-ray source and the longitudinal axis and (ii) a reference line, and the line and the reference line lie in a plane perpendicular to the longitudinal axis; and
   setting the position of the X-ray source on the CT scan according to the determined tube start angle prior to performing the scan.

2. The method of claim 1, wherein determining the tube start angle comprises the step of determining a number of tube rotations based on the location of the selected organ, the starting location of the X-ray source, the beam width of the CT scan, and the pitch of the CT scan, wherein the number of tube rotations is the number of tube rotations from the starting location of the X-ray source to the location of the selected organ.

3. The method of claim 2, wherein the number of tube rotations is determined using the equation R=(OLoc−SLoc)/(pitch×N), wherein:
 R is the number of tube rotations from the starting location of the X-ray source to the location of the selected organ;
 OLoc is the location of the selected organ centroid along the longitudinal axis;
 SLoc is the starting location of the X-ray source along the longitudinal axis;
 pitch is the pitch of the CT scan; and
 N is the beam width of the CT scan.

4. The method of claim 1, wherein the tube start angle is determined using a number of tube rotations, wherein the number of tube rotations is the number of tube rotations from the starting location of the X-ray source to the location of the selected organ.

5. The method of claim 4, wherein the tube start angle is determined using the equation TSA=OCTA−(360×(R−floor(R))), wherein:
 TSA is the tube start angle;
 OCTA is the angle of the X-ray source of the CT scan as it crosses the longitudinal center of the selected organ along the longitudinal axis;
 R is the number of tube rotations from the starting location of the X-ray source to the location of the selected organ; and
 floor(R) is the integer part of R.

6. The method of claim 5, further comprising determining the number of tube rotations R based on the location of the selected organ, the starting location of the X-ray source, the beam width of the CT scan, and the pitch of the CT scan.

7. The method of claim 6, wherein the number of tube rotations R is determined using the equation R=(OLoc−SLoc)/(pitch×N), wherein:
 OLoc is the location of the selected organ centroid along the longitudinal axis;
 SLoc is the starting location of the X-ray source along the longitudinal axis;
 pitch is the pitch of the CT scan; and
 N is the beam width of the CT scan.

8. The method of claim 1, wherein the location of the selected organ, the starting location of the X-ray source, the beam width of the CT scan, and the pitch of the CT scan are input into the computer using a graphical interface.

9. The method of claim 1, wherein the location of the selected organ is determined using a planning radiograph of the patient.

10. A system for reducing radiation dose for a selected organ on a patient, comprising:
 a computed tomography (CT) scan using an X-ray source that rotates around the patient as the patient is lying down on a patient bed being translated along a longitudinal axis through an X-ray gantry to scan the patient; and
 a computer configured to:
  determine a tube start angle relative to an orientation of the patient bed for the X-ray source of the CT scan based on a location of the selected organ along the longitudinal axis, a starting location of the X-ray source along the longitudinal axis, a beam width of the CT scan, and a pitch of the CT scan, wherein the tube start angle is defined by (i) a line between the X-ray source and the longitudinal axis and (ii) a reference line, and the line and the reference line lie in a plane perpendicular to the longitudinal axis; and
  set the position of the X-ray source on the CT scan is set based on according to the determined tube start angle prior to performing the scan.

11. The system of claim 10, wherein the computer is configured to determine the tube start angle by determining a number of tube rotations based on the location of the selected organ, the starting location of the X-ray source, the beam width of the CT scan, and the pitch of the CT scan, wherein the number of tube rotations is the number of tube rotations from the starting location of the X-ray source to the location of the selected organ.

12. The system of claim 11, wherein the computer is configured to determine the number of tube rotations using the equation R=(OLoc−SLoc)/(pitch×N), wherein:
 R is the number of tube rotations from the starting location of the X-ray source to the location of the selected organ;
 OLoc is the location of the selected organ centroid along the longitudinal axis;
 SLoc is the starting location of the X-ray source along the longitudinal axis;
 pitch is the pitch of the CT scan; and
 N is the beam width of the CT scan.

13. The system of claim 10, wherein the computer is configured to determine the tube start angle using a number of tube rotations, wherein the number of tube rotations is the number of tube rotations from the starting location of the X-ray source to the location of the selected organ.

14. The system of claim 13, wherein the computer is configured to determine the tube start angle using the equation TSA=OCTA−(360×(R−floor(R))), wherein:
 TSA is the tube start angle;
 OCTA is the angle of the X-ray source of the CT scan as it crosses the longitudinal center of the selected organ along the longitudinal axis;
 R is the number of tube rotations from the starting location of the X-ray source to the location of the selected organ; and
 floor(R) is the integer part of R.

15. The system of claim 14, wherein the computer is configured to determine the number of tube rotations R based on the location of the selected organ, the starting location of the X-ray source, the beam width of the CT scan, and the pitch of the CT scan.

16. The system of claim 15, wherein the computer is configured to determine the number of tube rotations R using the equation R=(OLoc−SLoc)/(pitch×N), wherein:
 OLoc is the location of the selected organ centroid along the longitudinal axis;
 SLoc is the starting location of the X-ray source along the longitudinal axis;
 pitch is the pitch of the CT scan; and
 N is the beam width of the CT scan.

17. The system of claim 10, wherein the CT scan is communicatively coupled to the computer.

18. The system of claim 10, wherein the computer is configured to provide a graphical interface that enables a user to input the location of the selected organ, the starting location of the X-ray source, the beam width of the CT scan, and the pitch of the CT scan.

19. A program storage device readable by a machine, tangibly embodying a program of instructions executable by the machine to perform a method of reducing radiation dose for a selected organ on a patient in a computed tomography (CT) scan that uses an X-ray source that rotates around the patient as the patient is lying down on a patient bed being translated along a longitudinal axis through an X-ray gantry to scan the patient, the method comprising:

determining a tube start angle between a direction of the X-ray source of the CT scan and an orientation of the patient bed or the patient lying down on the patient bed, based on a location of the selected organ along the longitudinal axis, a starting location of the X-ray source along the longitudinal axis, a beam width of the CT scan, and a pitch of the CT scan, wherein the tube start angle is defined by (i) a line between the X-ray source and the longitudinal axis and (ii) a reference line, and the line and the reference line lie in a plane perpendicular to the longitudinal axis; and setting the position of the X-ray source on the CT scan according to the determined tube start angle prior to performing the scan.

20. The device of claim 19, wherein determining the tube start angle comprises the step of determining a number of tube rotations based on the location of the selected organ, the starting location of the X-ray source, the beam width of the CT scan, and the pitch of the CT scan, wherein the number of tube rotations is the number of tube rotations from the starting location of the X-ray source to the location of the selected organ.

21. The device of claim 20, wherein the number of tube rotations is determined using the equation R=(OLoc−SLoc)/(pitch×N), wherein:

R is the number of tube rotations from the starting location of the X-ray source to the location of the selected organ;

OLoc is the location of the selected organ centroid along the longitudinal axis;

SLoc is the starting location of the X-ray source along the longitudinal axis;

pitch is the pitch of the CT scan; and

N is the beam width of the CT scan.

22. The device of claim 19, wherein the tube start angle is determined using a number of tube rotations, wherein the number of tube rotations is the number of tube rotations from the starting location of the X-ray source to the location of the selected organ.

23. The device of claim 22, wherein the tube start angle is determined using the equation TSA=OCTA−(360×(R−floor(R))), wherein:

TSA is the tube start angle;

OCTA is the angle of the X-ray source of the CT scan as it crosses the longitudinal center of the selected organ along the longitudinal axis;

R is the number of tube rotations from the starting location of the X-ray source to the location of the selected organ; and floor(R) is the integer part of R.

24. The device of claim 23, wherein the method further comprises determining the number of tube rotations R based on the location of the selected organ, the starting location of the X-ray source, the beam width of the CT scan, and the pitch of the CT scan.

25. The device of claim 24, wherein the number of tube rotations R is determined using the equation R=(OLoc−SLoc)/(pitch×N), wherein:

OLoc is the location of the selected organ centroid along the longitudinal axis;

SLoc is the starting location of the X-ray source along the longitudinal axis;

pitch is the pitch of the CT scan; and

N is the beam width of the CT scan.

26. The device of claim 23, wherein the centroid of the selected organ along the longitudinal axis is determined by averaging the longitudinal location of all voxels assigned to the selected organ.

* * * * *